(12) United States Patent
Knoth et al.

(10) Patent No.: US 8,603,945 B2
(45) Date of Patent: Dec. 10, 2013

(54) METHODS AND COMPOSITIONS FOR PROVIDING SALICYCLIC ACID-INDEPENDENT PATHOGEN RESISTANCE IN PLANTS

(75) Inventors: Colleen Marie Knoth, Costa Mesa, CA (US); Thomas Eulgem, Riverside, CA (US); Thomas Girke, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 169 days.

(21) Appl. No.: 13/055,363

(22) PCT Filed: Jul. 23, 2009

(86) PCT No.: PCT/US2009/051597
§ 371 (c)(1),
(2), (4) Date: Jun. 20, 2011

(87) PCT Pub. No.: WO2010/011871
PCT Pub. Date: Jan. 28, 2010

(65) Prior Publication Data
US 2011/0301035 A1 Dec. 8, 2011

Related U.S. Application Data

(60) Provisional application No. 61/083,154, filed on Jul. 23, 2008.

(51) Int. Cl.
*A01N 25/26* (2006.01)
*A01N 43/40* (2006.01)
*A01N 37/44* (2006.01)
*A61K 31/435* (2006.01)
*A61K 31/44* (2006.01)
*C07D 213/62* (2006.01)
*C07D 335/02* (2006.01)
*C07C 51/00* (2006.01)

(52) U.S. Cl.
USPC ........ 504/100; 504/116.1; 504/189; 504/244; 504/255; 504/260; 504/288; 504/320; 504/322; 504/323; 514/277; 514/344; 514/345; 514/352; 514/567; 546/261; 546/262; 546/263; 549/1; 549/13; 549/28; 558/411; 558/412; 562/405; 562/426; 562/433; 562/453

(58) Field of Classification Search
USPC .......... 514/567, 277, 344, 345, 352; 546/250, 546/261, 262, 263; 549/1, 13, 28; 558/411, 558/412; 562/405, 426, 433, 453
See application file for complete search history.

(56) References Cited

U.S. PATENT DOCUMENTS 5,661,183 A * 8/1997 Bjork et al. .................... 514/567
5,744,638 A * 4/1998 Schmand et al. .............. 562/456
(Continued)

FOREIGN PATENT DOCUMENTS

EP        0360417 A3 * 3/1990 ............ C07C 251/24
WO    20071090752 A1    8/2007
(Continued)

OTHER PUBLICATIONS

Conrath et al., "Two inducers of plant defense responses, 2,6-dichloroisonicotinic acid and salicylic acid, inhibit, catalyse activity in tobacco", 1995, Proc. Natl. Acad. Sci. USA; 92: 7143-7147.*

(Continued)

*Primary Examiner* — Jane C Osvvecki
(74) *Attorney, Agent, or Firm* — Joseph R. Baker, Jr.; Gavrilovich, Dodd & Lindsey LLP

(57) ABSTRACT

This disclosure relates to methods and compositions for modulating disease resistance in plants and transgenic plants.

16 Claims, 7 Drawing Sheets

(56) References Cited

U.S. PATENT DOCUMENTS

2003/0101487 A1 5/2003 Kisaka et al.
2007/0043068 A1 2/2007 Arnold et al.
2007/0130643 A1 6/2007 Kisaka et al.

FOREIGN PATENT DOCUMENTS

WO 20081001076 A1 1/2008
WO 20081017381 A1 2/2008
WO 2008/79988 A2 7/2008

OTHER PUBLICATIONS

Colson-Hanks et al., "Effect of 2,6-dichloroisonicotinic acid, its formulation materials and benzothiadiazole on systemic resistance to alternaria leaf spot in cotton", 2000; Plant Pathology, 49: 171-178.*
Becamel, Philippe. Preliminary Report on Patentability and Written Opinion, Date of Issuance of Report: Jan. 25, 2011, International Application Number: PCT/US2009/051597.
Jeong, Sei Joon, International Search Report, Korean Intellectual Property Office, PCT/US2009/051597, Sep. 28, 2010.

* cited by examiner

METHODS AND COMPOSITIONS FOR PROVIDING SALICYCLIC ACID-INDEPENDENT PATHOGEN RESISTANCE IN PLANTS

STATEMENT REGARDING FEDERALLY SPONSORED RESEARCH

This invention was made with Government support under Grant Nos. IOB 0449439 and IGERT #DGE 0504249 awarded by the National Science Foundation. The government has certain rights in this invention.

CROSS REFERENCE TO RELATED APPLICATIONS

This application is a U.S. National Stage Application filed under 35 U.S.C. §371, and claims priority to International Application No. PCT/US09/51597, filed Jul. 23, 2009, which claims priority to U.S. Provisional Application No. 61/083,154, filed Jul. 23, 2008, the disclosures of which are incorporated herein by reference.

TECHNICAL FIELD

This disclosure relates to methods and compositions for modulating disease resistance in plants and transgenic plants.

BACKGROUND

Strong resistance of plants to pathogenic microorganisms is often mediated by disease resistance (R) genes which allow specific molecular recognition of invading organisms (Dangl and Jones, 2001). They trigger a wide variety of defense reactions. In addition, R-independent mechanisms can activate basal defense reactions limiting the extent of infections (Chisholm et al., 2006). Recognition of pathogens by R-dependent or R-independent mechanisms activates partially overlapping defense programs that include coordinated transcriptional re-programming of large sets of genes (Eulgem et al., 2004; Eulgem, 2005). A key signaling molecule mediating R-dependent and R-independent disease resistance is salicylic acid (SA).

Salicylic acid (SA) is signal molecule in the deployment of systemic acquired resistance (SAR). After the initial observation that exogenous application of SA induces resistance in tobacco, SA has been shown to induce resistance in many plant species. Exogenous application of SA also induces expression of the same class of pathogenesis-related (PR) (PR-1, BCL2 (PR-2), and PR-5) genes as those induced during SAR. A strong correlation has been observed between the in vivo increase in SA levels in infected plants and both the expression of PR genes and development of resistance. In addition, SA appears to be involved in the activation of HR cell death and restriction of pathogen spread. The strongest evidence supporting the signaling role of SA in plant defense comes from studies on plants unable to accumulate SA upon pathogen infection. For example, transgenic tobacco and *Arabidopsis* plants constitutively expressing the *Pseudomonas putida* nahG gene, which encodes the SA-degrading enzyme salicylate hydroxylase, fail to develop SAR and are hypersusceptible to pathogen infection. Likewise, preventing SA accumulation by application of SA biosynthesis inhibitors also makes otherwise resistant *Arabidopsis* plants susceptible to *Hyaloperonospora parasitica*. Conversely, the elevated levels of SA present in the *Arabidopsis* acd (accelerated cell death; Greenberg et al. 1994; Rate et al. 1999), lsd (lesion simulating disease; Dietrich et al. 1994; Weymann et al. 1995), cpr (constitutive expressor of PR genes; Bowling et al., 1994, 1997; Clarke et al. 1998; Silva et al. 1999), ssi (suppressor of salicylate insensitivity of npr1-5; Shah et al. 1999), and dnd (defense with no HR cell death; Yu et al. 1998) mutants lead to constitutive expression of PR genes and SAR.

SUMMARY

The disclosure demonstrates that pathogenic interactions between the higher plant *Arabidopsis thaliana* (*Arabidopsis*) and isolates of the strict biotrophic oomycete *Hyaloperonospora parasitica* (*Peronospora*; Hp; (Slusarenko and Schlaich, 2003) are useful to dissect defense-associated signaling networks controlling transcriptional reprogramming in plants. *Peronospora* and related species within the family of Peronosporaceae cause very destructive plant diseases, called downy mildews, of dicotyledonous plants including grapes, cucurbitis species, onion, garlic and spinach, that are very important for the U.S. agriculture (Agrios, 1997).

The disclosure provides compositions and methods useful to prevent and treat infection in plants. The compounds of the disclosure are small bioactive organic molecules that interfere with regulatory mechanisms of the plant immune system and transcriptionally induce defense genes as well as disease resistance. These novel synthetic elicitors are useful in the development of new pesticides.

The disclosure provides a compound of general formula I:

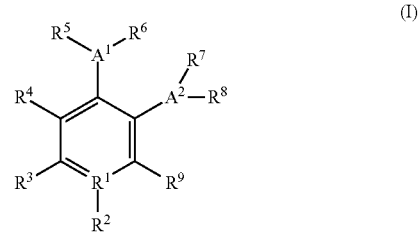

wherein $R^1$ is C, N or S; wherein $R^2$ and $R^4$ are each independently a hydrogen, oxygen, sulfide, alkyl, hydroxyl, alkoxide, amino, mercapto, alkyl sulfide, thionyl, halo, cyano, nitro or carboxylate; wherein at least one of $R^3$ and $R^9$ is a halogen and wherein $R^3$ and $R^9$ can be a hydrogen, alkyl, oxygen, halo or mercapto; wherein $A^1$ and $A^2$ are each independently a carbon, nitrogen, oxygen or sulfur, wherein when $A^1$ or $A^2$ is a nitrogen, $R^5$, $R^6$, $R^7$ or $R^8$ is a hydrogen, wherein when $A^1$ comprises a carbon, $A^1$ comprises —COOH or a carboxyalkyl and $A^2$ is —NHR$^8$ wherein $R^8$ is —H, or an alkyl and wherein a structure of compound I induces modulation of expression of a resistance gene or a gene from Table I or induces pathogen or disease resistance in a plant. In one embodiment, $A^1$ and $A^2$ are each independently carbon or nitrogen; wherein at least one of $R^3$ or $R^9$ is a chloro-, iodo- or bromo-group. In yet another embodiment, the compound comprises general formula II:

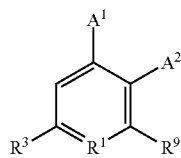

(II)

wherein R¹ is C or N, R³ and R⁹ are each individually selected from chloro, bromo or iodo group; wherein A¹ is a —COOH or a carboxyalkyl and A² is —NHR⁸ wherein R⁸ is —H, or an alkyl. In yet another embodiment, the compound comprises a formula III:

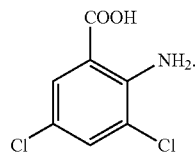

(III)

The compounds of the disclosure can be formulated for delivery to an environment, agricultural environment, plant and the like. In some embodiments, the compound can be formulated with one or more other active ingredients such as, for example, salicylic acid.

The disclosure also provides a method of providing pathogen resistance in a plant comprising contacting the plant with a compound of the disclosure such that the compound induces expression of one or more resistance genes or one or more genes from Table 1.

The disclosure also provides a method for modulating expression of a gene in Table 1, comprising contacting a plant cell with an effective amount of a compound of formula I, II, or III.

The disclosure also provides a method of inducing pathogen resistance in a plant comprising contacting the plant with a compound having the general formula I:

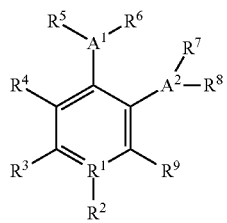

(I)

wherein R¹ is C, N or S; wherein R² and R⁴ are each independently a hydrogen, oxygen, sulfide, alkyl, hydroxyl, alkoxide, amino, mercapto, alkyl sulfide, thionyl, halo, cyano, nitro or carboxylate; wherein at least one of R³ and R⁹ is a halogen and wherein R³ and R⁹ can be a hydrogen, alkyl, oxygen, halo or mercapto; wherein A¹ and A² are each independently a carbon, nitrogen, oxygen or sulfur, wherein when A¹ or A² is a nitrogen, R⁵, R⁶, R⁷ or R⁸ is a hydrogen, wherein when A¹ comprises a carbon, A¹ comprises —COOH or a carboxyalkyl and A² is —NHR⁸ wherein R⁸ is —H, or an alkyl and wherein a structure of compound I induces modulation of a resistance gene, a gene from Table I or induces pathogen or disease resistance in a plant.

In one embodiment, A¹ and A² are each independently carbon or nitrogen; wherein at least one of R³ or R⁹ is a chloro-, iodo- or bromo-group. In yet another embodiment, the compound comprises general formula II:

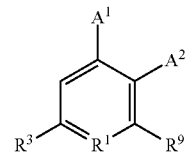

(II)

wherein R¹ is C or N, R³ and R⁹ are each individually selected from chloro, bromo or iodo group; wherein A¹ is a —COOH or a carboxyalkyl and A² is —NHR⁸ wherein R⁸ is —H, or an alkyl. In yet another embodiment, the compound comprises a formula III:

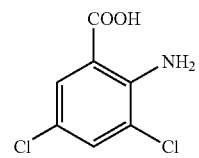

(III)

wherein the agent increases the production or transcription of a resistance gene. In yet another embodiment, the resistance gene comprises a LURP gene member. In a further embodiment, the compound causes an increase in expression of LURP genes and an SA-independent constitutive expression of PR genes.

The disclosure further provides a transgenic plant that comprises a DCA-responsive promoter region operably linked to a heterologous polynucleotide, wherein contact of the transgenic plant with a compound of formula I, II, or III causes expression or transcription of the heterologous polynucleotide. In one embodiment, the DCA-responsive promoter comprises a CaBP22 promoter region.

The disclosure also provides a method of inducing pathogen resistance in a plant comprising contacting the plant with a 3-, 4-, or 5-chloroanthranilic acid.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
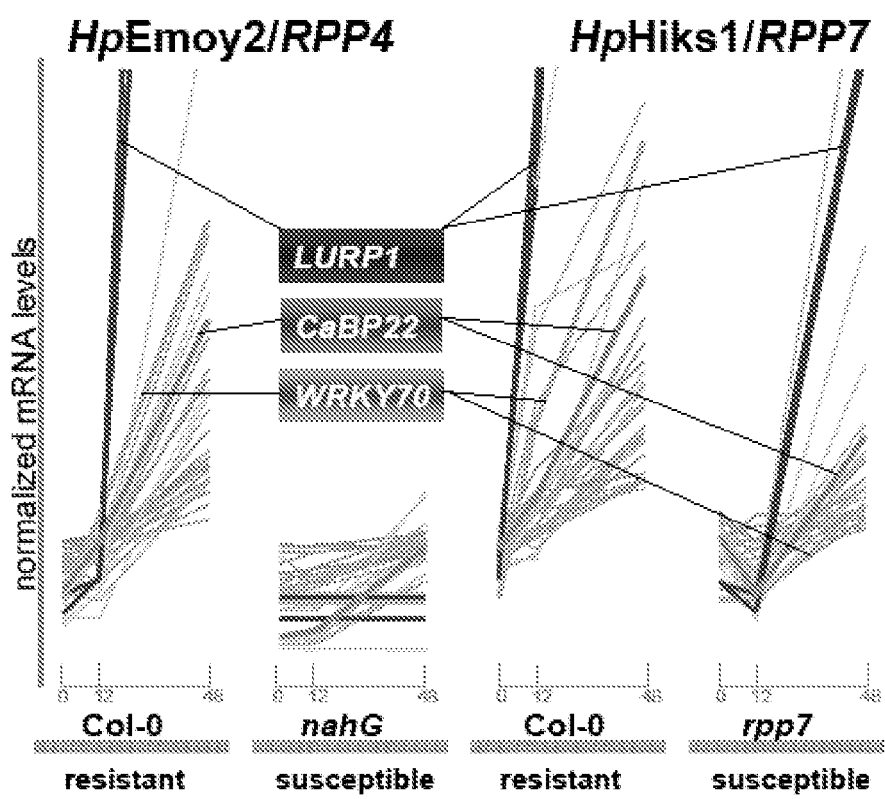
FIG. 1 shows an expression profile of *Arabidopsis* LURP genes after infection with *Peronospora*. Normalized transcript levels of LURP genes in Col-0, nahG or rpp7 plants at 0, 12 or 48 h post infection with the *Peronospora* isolates HpEmoy2 or HpHiks1. The shown data are derived from a study using Affymetrix *Arabidopsis* genome arrays (Eulgem et al., 2004). Similar results were obtained in an independent study using Affymetrix custom *Arabidopsis* whole genome arrays (Eulgem et al., 2007). nahG plants are compromised in basal defense and RPP4-mediated resistance; the rpp7 mutant has intact basal defense, but is compromised in RPP7-mediated *Peronospora* recognition. Col-0 plants contain RPP4 and RPP7.
Figure 2:
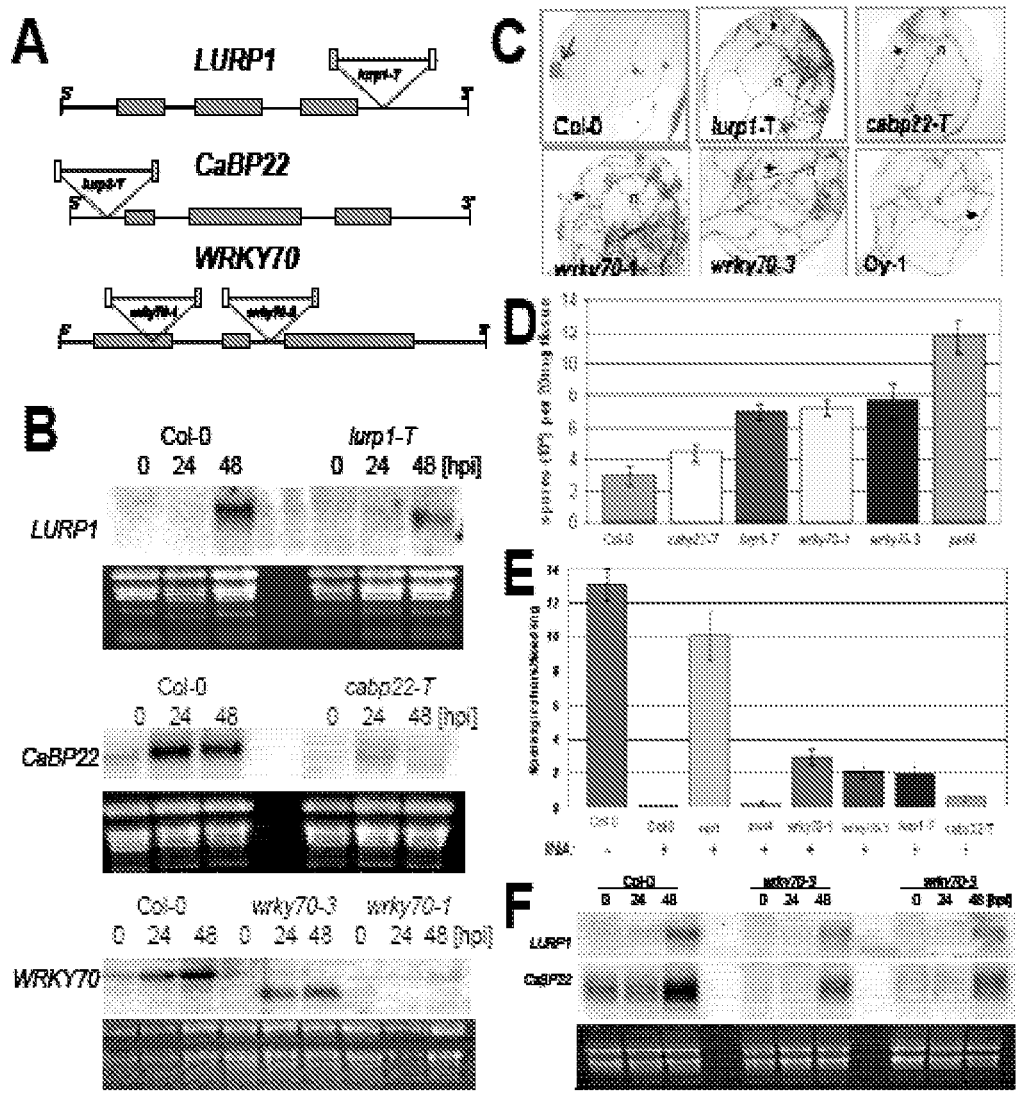
FIG. 2A-F shows analyses of lurp T-DNA mutants. A: Position and orientation of T-DNA insertions in lurp T-DNA mutants. T-DNA boarders are represented by open (right boarder) and filled (left boarder) boxes. Grey boxes signify exons, lines are introns. B: RNA gel blot analysis of LURP1, CaBP22 and AtWRKY70 expression in wildtype (Col-0) and T-DNA insertion mutants 0, 24 and 48 hours after infection with HpEmoy2 (5E4 spores/ml suspension). The ethidium bromide (Et-Br) stained RNA gel was photographed as loading control. C: Col-0 (resistant; wild-type), Oy-1 (susceptible control), and lurp mutants were stained with Trypan Blue 7 days after spraying with 5E4 spores of HpEmoy2/mL to visualize hyphal growth (bold black arrows) and cell death (HR) responses (red arrows). After infection with HpEmoy2, hyphae grew past the penetration site but were surrounded by a trail of necrotic plant cells (n; thin arrows) in lurp mutants. Col-0 had discrete HR sites. D: Effects of lurp mutations on basal defense. Plants were sprayed with virulent HpNoco2 (3E4 spores/ml). Spores were counted 7 dpi. Mean and standard error were calculated from 3 independent experiments. E: Effects of lurp mutants on resistance mediated by 2,6-dichloroisonicotinic acid (INA). Two-week-old seedlings were sprayed with 0.33 mM INA and incubated 2 days before spraying with HpNoco2 (3E4 spores/ml). Spores were counted 7 days after HpNoco2 infection. Significantly more sporangiophores were counted on the lurp mutants than Col-0 after INA treatment. F: RNA gel blot analyses of LURP1, CaBP22 transcripts in Col-0 and wrky70 mutants 0, 24 and 48 hpi with HpEmoy2 (5E4 spores/ml). The Et-Br-stained RNA gel is shown as loading control.
Figure 3:
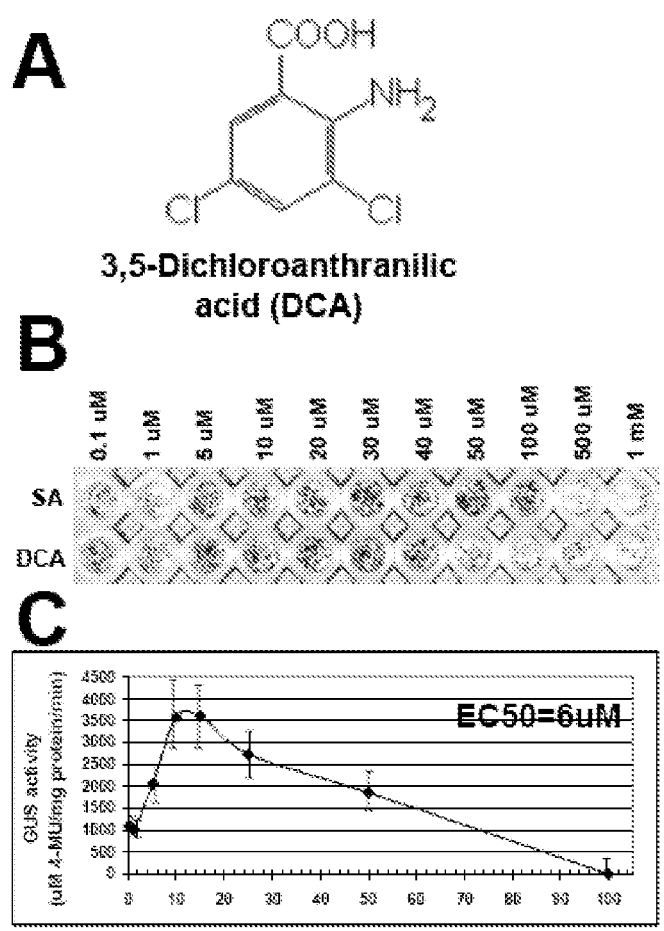
FIG. 3A-C shows DCA is a potent inducer of 333_CaBP22::GUS in Arabidopsis. A: Structure of DCA. B/C: Dose-response curves. One-week old –333_CaBP22::GUS seedlings were grown in liquid medium and incubated with the indicated concentrations of DCA (67) or SA for 24 h prior to Xgluc staining (blue, panel B) or quantitative assays for GUS activity using 4-methyl umbelliferyl-glucuronide (MUG, panel C).

As used herein and in the appended claims, the singular forms "a," "and," and "the" include plural referents unless the context clearly dictates otherwise. Thus, for example, reference to "a compound" includes a plurality of such compounds and reference to "the plant" includes reference to one or more plants known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Recognition of a pathogen by a plant triggers a cascade of responses in plants. Recognition frequently involves strain-specific detection of a pathogen-encoded elicitor, through direct or indirect interaction, with the corresponding resistance (R) gene product. Such an interaction (also known as incompatible interaction) triggers one or more defense signaling cascades and is often associated with induction of hypersensitive response (HR) at the site of pathogen entry. HR is one of the first visible manifestations of the host-induced defense response and is thought to help prevent multiplication and movement by confining the pathogen to dead cells. An "R" gene-mediated recognition of pathogen can also lead to the accumulation of various phytohormones, which in turn signal activation of defense gene expression. Each hormone activates a specific pathway wherein the genes act individually, synergistically or antagonistically, depending upon the pathogen involved, and a combined effect of which confers resistance and prevents spread of the pathogen to uninoculated parts of the plants.

Resistance (R) gene-dependent defense signaling in plants is often mediated by the plant hormone salicylic acid (SA) and requires the function of several downstream components.

Recognition of biotrophic pathogens triggers complex defense programs resulting in extensive transcriptional reprogramming (Eulgem 2005; Katagiri 2004; Somssich and Hahbrock 1998). Genes upregulated during plant immune responses can have important roles for disease resistance (Bartsch et al. 2006; Ramonell et al. 2005; Rowland et al. 2005; Veronese et al. 2006).

At least two mechanisms of pathogen recognition are used by plants. Perception of chemical signatures ubiquitously present in large classes of pathogens can activate basal defense, which restricts growth of a wide range of pathogens (Chisholm et al. 2006; Nürnberger et al. 2004). In addition, disease resistance (R) genes direct detection of distinct pathogen races by genetically interacting with pathogen-derived avirulence (avr) genes. "R" protein engagement triggers strong "gene-for-gene" resistance, resulting in incompatible plant-pathogen interactions (plant resistant, pathogen avirulent) (Dangl and Jones 2001; Flor 1971). A hallmark of R-mediated resistance is the hypersensitive response (HR), a programmed death of plant cells at infection sites. Absence of R-mediated recognition gives rise to compatible interactions and the development of disease symptoms (plant susceptible, pathogen virulent) (Hammond-Kosack and Parker 2003). Basal defense responses, however, can be active during compatible interactions (Glazebrook 2001; Glazebrook et al. 1996).

Several components of the SA-mediated pathway have been identified and mutations in these pathway components lead to enhanced susceptibility to various pathogens. Mutations in eds1 (a putative lipase), eds5 (a member of the MATE transporter family), pad4 (a putative lipase) and sid2 (an isochorismate synthase), lower or abolish pathogen-induced increase in SA levels. The EDS1, EDS5, PAD4 and SID2 proteins participate in both basal resistance to virulent pathogens as well as R protein-mediated response to avirulent pathogens. Resistance signaling mediated via a majority of R proteins that contain Toll-interleukin1-like (TIR) domains at their N-terminal end is dependent on EDS1. However, a few R proteins containing coiled coil (CC) domains at their N-terminal end are also dependent on EDS1. This includes HRT, which confers resistance to Turnip Crinkle Virus and RPW8, which confers broad-spectrum resistance to powdery mildew. However, RPW8 is not a nucleotide binding (NB)-leucine rich repeat (LRR) type R protein, instead it contains a N-terminal transmembrane domain in addition to the CC domain.

Microarray studies suggested that differences between gene-for-gene resistance and basal defense in *Arabidopsis thaliana* are quantitative rather that qualitative (Eulgem et al. 2004; Maleck et al. 2000; Navarro et al. 2004; Tao et al. 2003). Katagiri and coworkers proposed that R-mediated pathogen recognition can boost basal defense reactions, resulting in accelerated and more intense responses (Katagiri 2004; Tao et al. 2003). This quantitative signaling mechanism may involve coordinated production of the reactive oxygen intermediates (ROI) $O_2^-$, $H_2O_2$, and NO as well as salicylic acid (SA) (Delledonne et al. 2002; Durner and Klessig 1999; Torres and Dangl 2005). SA triggers downstream signaling processes activating defense-associated genes as well as systemic acquired resistance (SAR) (Klessig et al. 2000; Maleck et al. 2000; Schenk et al. 2000).

In *Arabidopsis*, both basal defense and SAR are dependent on SA as well as NPR1, a nuclear transported transcriptional cofactor (Cao et al. 1994, 1997; Kinkema et al. 2000; Mou et al. 2003; Ryals et al. 1997). While application of SA (White 1979) or its functional analog 2,6-dichloroisonicotinic acid (INA) (Kessmann et al. 1993; Uknes et al. 1992) effectively induce SAR and basal defense, blocking of SA accumulation by mutations in PAD4 or overexpression of a bacterial SA hydroxylase gene (nahG) abolish these defense responses (Delaney et al. 1994; Jirage et al. 1999; Nawrath et al. 2002; Wildermuth et al. 2001). Mutations in NPR1 also block basal defense and SAR, including many SA- or INA-inducible responses, indicating a role of NPR1 downstream from SA (Dong 2004).

Several *Arabidopsis* transcription factors, including members of the large family of WRKYs, have been implicated in defense signaling (Dong et al. 2003; Eulgem et al. 2000; Maleck et al. 2000; Ulker and Somssich 2004; Wu et al. 2005). The defining feature of WRKYs is the conserved DNA binding domain of approximately 60 amino acids containing the nearly invariant stretch WRKYGQK followed by a unique zinc-finger pattern of Cys and His residues (Rushton et al. 1996). WRKYs were subdivided into three groups (Eulgem et al. 2000). Members of group I have two WRKY domains, whereas members of groups II and III have one WRKY domain. Group III WRKY domains contain a Cx7CX23HXC pattern of zinc ligands which is distinct from the Cx4-5CX22-23HXH zinc finger pattern of group I and II WRKY domains. Mutations in either the WRKYGQK or the zinc finger motif of WRKY domains compromised their DNA binding ability (Maeo et al. 2001). Most WRKYs seem to interact specifically with a DNA motif termed W box (TTGACC/T).

The nearly ubiquitous presence of W boxes in promoters of defense-associated genes strongly suggests a broad role of WRKY factors in resistance to pathogens (Chen et al. 2002; Dong et al. 2003; Eulgem et al. 2004; Maleck et al. 2000; Navarro et al. 2004; Ramonell et al. 2002). Overexpression of defined *Arabidopsis* WRKY (AtWRKY) genes altered resistance to pathogenic bacteria or fungi (Asai 2002; Chen and Chen 2002; Li et al. 2004). Silencing of three separate WRKY genes in tobacco reduced resistance to Tobacco mosaic virus mediated by the R gene N (Liu et al. 2004). The *Arabidopsis* gene RRS1-R encodes an atypical group III WRKY (AtWRKY52) with structural features of R proteins that confers resistance to several strains of *Ralstonia solanacearum* (Deslandes et al. 2002, 2003). A recent study revealed complex functions in disease resistance for the structurally related AtWRKY18, AtWRKY40, and AtWRKY60 proteins (Xu et al. 2006). These proteins were shown to have partially redundant roles in activating defense to the fungal necrotroph *Bot-*

*rytis cinerea* and repressing basal resistance to a virulent strain of the bacterial hemibiotroph *Pseudomonas syringae*. Complex roles also were demonstrated for AtWRKY70, encoding a group III WRKY protein. Although AtWRKY70 contributes to basal resistance to the virulent biotrophic fungus *Erysiphe chicoracearum*, it represses defenses to the fungal necrotroph *Alternaria brassicicola* (Li et al. 2004, 2006). Unlike resistance to biotrophy, which frequently is mediated by SA, resistance to necrotrophs has been associated with jasmonic acid (JA) (Glazebrook 2001). Multiple studies have demonstrated antagonistic crosstalk between SA and JA signaling (Glazebrook et al. 2003; Kunkel and Brooks 2002; Petersen et al. 2000; Spoel et al. 2003). AtWRKY70 serves as an activator of SA-inducible pathogenesis-related (PR) genes and a repressor of the JA-inducible gene PDF2-1; therefore, it was suggested to have a role in determining the balance between SA and JA signaling (Li et al. 2004, 2006). Furthermore, epistasis analyses indicated that AtWRKY70 operates downstream from defense-associated SA accumulation as well as downstream or independent from NPR1.

AtWRKY70 contributes to the regulation of the LURP cluster, a set of *Arabidopsis* genes that are co-expressed in response to infection with *Peronospora*. The disclosure shows that two members of the LURP cluster, LURP1 and CaBP22, encode components of an important defense mechanism. LURP expression appears to be controlled by a multitude of defense regulators including AtWRKY70 and other transcription factors. The SA-independent disease protective methods and compositions of the disclosure can be used on plant crops to treat or reduce the risk of disease. Based on the results of the disclosure a compound comprising general formula I, II and formula III, salts and analogs thereof provide useful pesticide agents to fight plant diseases by enhancing the plant's inherent defense capabilities. Such plant immune stimulators are non-toxic and expected to be more environmentally friendly. The performance of a compound of formula I, II or III may be further improvable by the design of derivatives that allow for more efficient uptake by the plant. An exemplary structure and modifications are provided by formula I. The compound of formula III is shown to specifically target a subset of plant immune responses (an AtWRKY70-dependent signaling branch), and can act in a synergistic fashion with other defense inducers that activate additional parts of the plant immune system.

The disclosure provides a compound with general formula I, useful for inducing pathogen or disease resistance in a plant.

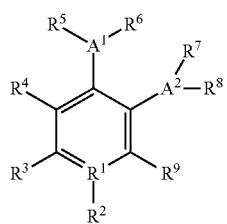

(I)

wherein R1 is C, N or S; wherein R2 and R4 are each independently a hydrogen, oxygen, sulfide, alkyl, hydroxide, alkoxide, amino, mercaptor, alkyl sulfide, thionyl, halo, cyano, nitro or carboxylate; wherein at least one of R3 and R9 is a halogen and wherein R3 and R9 can be a hydrogen, alkyl, oxygen, halo or mercapto; wherein A1 and A2 are each independently a carbon, nitrogen, oxygen or sulfur, wherein when A1 or A2 is a nitrogen, R5, R6, R7 or R8 is a hydrogen, wherein when A1 comprises a carbon, A1 comprises —COOH or a carboxyalkyl and $A^3$ is —NHR$^{10}$ wherein R$^{10}$ is —H, or an alkyl and wherein a structure of compound I induces modulation of a gene from Table I or induces pathogen or disease resistance in a plant. In yet another embodiment, the disclosure provides a mono- or di-halogenated anthralinic acid. The disclosure provides compound having the general formula II:

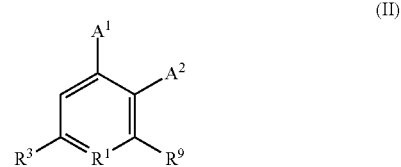

(II)

wherein $R^1$ is C or N, $R^3$ and $R^9$ are each individually selected from chloro, bromo or iodo group; wherein $A^1$ is a —COOH or a carboxyalkyl and $A^2$ is —NHR$^{10}$ wherein R$^{10}$ is —H, or an alkyl.

In another embodiment, the compound comprises a formula III (DCA):

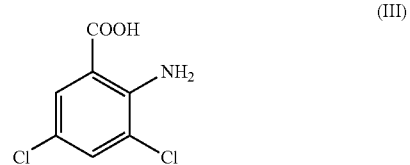 [SMILES: Nc1c(Cl)cc(Cl)cc1C(=O)O]

(III)

wherein the compound increases the extent of defense gene transcription.

The disclosure further encompasses, salts and analogs of any of the foregoing. In yet another aspect, the compounds are formulated for topical administration to the leaf of a plant and can include pharmaceutically acceptable carriers.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. The term cyclopentyl ring refers to a ring of five carbons with any degree of unsaturation. The term cyclohexyl ring refers to a ring of six carbons with any degree of unsaturation.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of R1-R5 together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more $CH_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO2R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;
- —SO$_2$N(R)$_2$ where R is a hydrogen, an alkyl group, or an aryl group and R and R can form a ring;
- —OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl⁻, Br⁻), sulfate, acetates (e.g., acetate, trifluoroacetate), ascorbates, aspartates, benzoates, citrates, and lactate.

Compounds of the disclosure can have prodrug forms. Prodrugs of the compounds of the invention are useful in the methods of this invention. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Contact with a crop or plant cell with a compound as described herein results in an increase in transcript levels of defined defense genes (e.g., LURP genes) and confers resistance to disease causing pathogens or agents. This alternative pathway does not require SA or other defense components that are generally required for resistance.

Accordingly, the disclosure provides methods and compositions that provide an alternative pathway for disease resistance independent of SA-induced resistance. Such methods and compositions are useful to broaden disease resistance in plant types including those that comprise a mutant resistance pathway resulting in a dysfunctional disease resistance. In addition, wherein there exists and active SA-mediated resistance pathway, addition of the compounds of the disclosure and methods of use as described herein results in an additive, more effective, disease resistance in plants.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in the method of the disclosure is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence or a modulating nucleic acid (e.g., an antisense, an siRNA or ribozyme) operably linked (i.e., under regulatory control of) to an appropriate inducible or constitutive regulatory sequences that allow for the expression of a polypeptide or modulating nucleic acid. The expression cassette can be introduced into a plant by transformation or by breeding after transformation of a parent plant. Such methods can be used in a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell. For example, in one embodiment, the disclosure provides an expression cassette comprising a CaBP22 promoter region operably linked to a heterologous polynucleotide. The expression cassette can be used in an expression system, whereby induction of transcription by the promoter can be induced by contact with a compound of Formula I, II or III. Accordingly, transgenic plants comprising an expression cassette of the disclosure can be induced to express a desired gene or polynucleotide upon contact with a compound of formula I, II or III.

In another embodiment, the disclosure provides a method for protecting a plant from a pathogen comprising applying an effective amount of a compound of formula I, II or III (e.g., DCA) that modulates the expression of a LURP gene (e.g., CaBP22). "Effective amount" is intended to mean a compound or composition sufficient to control a pathogen. A compound of the disclosure that promotes LURP gene expression can be applied to the environment of the pathogen by methods known to those of ordinary skill in the art.

A composition of the disclosure comprising a compound of formula I, II or III may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present disclosure are normally applied in the form of compositions and can be applied to the crop area, plant, or seed to be treated. For example, the compositions of the present disclosure may be applied during growth, seeding or storage.

The compositions of the disclosure may be applied simultaneously or in succession with other compounds. Methods of applying an active ingredient of the present disclosure or an agrochemical composition of the present disclosure that contains at least one of a compound of formula I, II or III include, but are not limited to, foliar application, seed coating, and soil application. The number of applications and the rate of application depend on the intensity of infestation by the corresponding pathogen.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluent before application. The concentration of a compound of the disclosure will vary depending upon the nature of the particular formulation, specifically, whether it is a concentrate or to be used directly.

A compositions of the disclosure can be applied to the environment of a plant or plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. It is generally important to obtain good control of pathogens in the early stages of plant growth, as this is the time when the plant can be most severely damaged. The compositions of the disclosure can conveniently contain an insecticide if this is thought necessary.

Compositions of the disclosure find use in protecting plants, seeds, and plant products in a variety of ways. For example, the compositions can be used in a method that involves placing an effective amount of the composition in the environment of the plant or pathogen by a procedure selected from the group consisting of spraying, dusting, broadcasting, or seed coating.

The methods of the embodiments may be effective against a variety of plant pathogens, such as, but not limited to, *Colletotrichum graminocola, Diplodia maydis, Verticillium dahliae, Fusarium graminearum, Fusarium oxysporum* and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Glomerella glycines, Phakopsora pachyrhizi, Pythium aphanidermatum, Pythium ultimum, Pythium debaryanum, Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striates, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana, Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, Sunflower: *Plasmopora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium verticillioides* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride, Claviceps sorghi, Pseudomonas avenae, Erwinia chrysanthemi* pv. *zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Sorghum: *Exserohilum turcicum, C. sublineolum, Cercospora sorghi, Gloeocercospora sorghi, Ascochyta sorghina, Pseudomonas syringae* p.v. *syringae,*

Xanthomonas campestris p.v. holcicola, Pseudomonas andropogonis, Puccinia purpurea, Macrophomina phaseolina, Perconia circinata*, *Fusarium verticillioides*, *Alternaria alternata*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari*, *Sporisorium reilianum* (*Sphacelotheca reiliana*), *Sphacelotheca cruenta*, *Sporisorium sorghi*, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*, etc.

The following examples are intended to illustrate but not limit the disclosure.

EXAMPLE

By microarray experiments several clusters of *Arabidopsis* genes exhibiting coordinated expression after *Peronospora* recognition mediated by the R genes RPP4 or RPP7 (Eulgem et al., 2004) were identified. The cluster of LURP (late upregulated in response to *Peronospora* recognition) genes exhibits a particularly pronounced coordinated increase of transcript levels after triggering RPP4 or RPP7 (FIG. 1). While RPP4 mediates SA-dependent resistance to the *Peronospora* isolate Emoy2 (HpEmoy2), RPP7 triggers resistance to the *Peronospora* isolate Hiks1 (HpHiks1) independently of SA (McDowell et al., 2000; van der Biezen et al., 2002). LURP transcripts levels typically exhibit a continuous steep increase over the first 48 hours post infection (hpi; FIG. 1). Accumulation of LURP transcripts is delayed or attenuated in susceptible lines lacking RPP4 or RPP7 function, which suggested a role of LURP genes in resistance to *Peronospora*. The highly coordinated nature of their expression further suggested that LURP genes are controlled by common regulatory mechanisms. In order to examine such mechanisms of LURP regulation three representative members of this gene set, LURP1 (At2g14560), CaBP22 (At2g41090) and AtWRKY70 (At3g54600) were examined.

To examine roles of LURPs in disease resistance, T-DNA mutants of these representative members (FIGS. 2A and B) were analyzed. While RPP7-resistance appeared not to be affected by any of the tested mutations, RPP4-resistance, basal defense and resistance mediated by the SA-analog INA are reduced in lurp mutants (FIGS. 2C, D and E). This suggested that LURPs operate in a SA-dependent pathway that is commonly utilized by R-mediated resistance and basal defense. By RNA blotting LURP1 and CaBP22 transcript levels were determined to be reduced in the wrky70 mutant alleles (FIG. 2F and Knoth et al., 2007). This suggested a possible (direct or indirect) role of the AtWRKY70 transcription factor in the regulation of LURP1, CaBP22 and other LURPs.

Reporter gene assays in transgenic *Arabidopsis* plants with promoter fragments fused to the β-glucuronidase gene (GUS) allowed identification of short LURP promoter stretches mediating responsiveness to *Peronospora*. The shortest responsive CaBP22 promoter fragment tested so far reaches up to position −333 (−333_CaBP22::GUS). The next shorter fragment that reaches up to position −65 does not mediate any reporter gene expression, defining a minimal responsive CaBP22 promoter region of 268 bp. This minimal responsive stretch of the CaBP22 promoter does not contain any binding sites of known transcription factors. However, this stretch bears two copies of a sequence related to the TL1 element, a defense-associated promoter element recently described (Wang et al., 2004). As the identification of transcription factors interacting with TL1 has not been reported yet, the minimal responsive CaBP22 promoter is likely to interact with so far unknown defense regulators.

Results described above showed that LURP1 and CaBP22 encode components of an important defense mechanism. LURP expression appears to be controlled by a multitude of defense regulators including AtWRKY70 and so far unknown transcription factors. Hence, a large number of potential protein targets for bioactive compounds seem to be acting upstream from LURPs. Thus LURP-promoter/reporter systems are useful tools to screen for defense inducing chemicals. A 333_CaBP22::GUS line was used to screen chemical libraries of the Center for Plant Cell Biology at UC-Riverside for substances that induce activity of this reporter in the absence of pathogens. One week old seedlings of the reporter line grown in 96 well plates with liquid MS medium were treated with library chemicals at a final concentration of 4-20 microM in 0.001% DMSO and stained with X-Gluc to detect GUS activity 24 h later (FIG. 2). The library chemicals were transferred from 384 well plates to the 96 well screening plates by a "96 pin-tool" using a pipetting robot. Screening of 22,000 compounds resulted in the identification of 49 substances that reproducibly induced activity of our reporter system.

Most of the identified −333_CaBP22::GUS-inducers are structurally related to the defense hormone salicylic acid (SA). One of these compounds, 3,5-Dichloroanthranilic acid (DCA, FIG. 3A) to be particularly efficient in inducing −333_CaBP22::GUS expression. The chemical structure of this compound was confirmed by NMR and MS analyses. DCA is a more potent inducer of −333_CaBP22::GUS than SA, as it is active at 10-fold lower concentrations (0.1 uM; FIG. 3B). Thus, DCA has a high specificity for its cellular target. Consistent with this the $EC_{50}$ value (effective concentration leading to a half-maximal response) of DCA is 6 uM (FIG. 3C), which is lower than the published EC50 value for PR1 induction by SA and its functional analog INA (65 and 10 uM, respectively; Wendehenne et al., 1998; Pillonel, 2001).

DCA-induced disease resistance against virulent *Peronospora* (FIG. 5A). For these experiments DCA had to be sprayed on aerial parts of soil grown seedlings. Efficient induction of disease resistance at DCA concentrations as low as 10 uM was demonstrated. Two batches of DCA from different sources had the same activity in the assays. The data indicate that DCA is a more potent inducer of −333_CaBP22::GUS than SA, as it is active at 10-fold lower concentrations (0.1 uM; FIG. 3B). Thus, DCA has a high specificity for its cellular target. Consistent with this the EC50 value (effective concentration leading to a half-maximal response) of DCA is 7 uM (FIG. 2C), which is lower than the published EC50 value for PR1 induction of SA and its functional analog INA (65 and 10 uM, respectively) (Wendehenne et al., 1998; Pillonel, 2001).

Semiquantitative RT-PCRs showed that 10 uM DCA, which efficiently induces expression of −333_CaBP22::GUS (FIG. 3C), also activates the endogenous CaBP22 gene and WRKY70 (FIG. 4). Most *Arabidopsis* mutants with deficiencies in defense signaling exhibited wild type expression of CaBP22 and WRKY70 in response to DCA treatment. In addition, the nahG transgene which expresses an SA-catabolizing enzyme does not suppress the inducing effect of DCA on CaBP22 and WRKY70. As the CaBP22-induction by DCA is blocked in the wrky70 mutant, this compound can interfere with a signaling component that acts upstream from WRKY70 transcription and either independently of downstream from SA. Based on this DCA targets a WRKY70-dependent branch of the defense signaling network.

Figure 4:
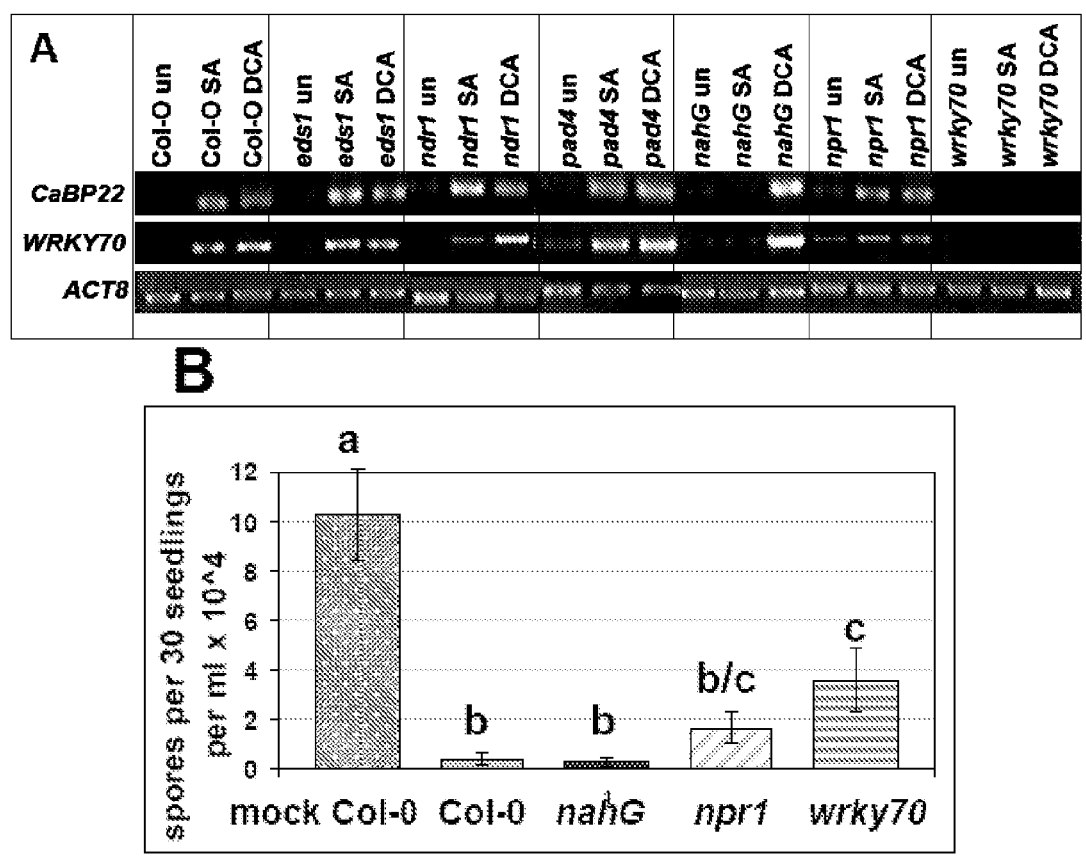
FIG. 4A-B shows DCA targets a WRKY70-dependent branch of the defense signaling network. (A) RT-PCR analysis of CaBP22 and WRKY70 expression in Col-0 (wild type) and mutant backgrounds 24 hours after spraying 2 week old seedlings with water (un), 1 mM SA, or 100 μM DCA. ACT8 is shown as loading control. At least three biological replicates showed consistent results. (B) Two week old seedlings were sprayed with virulent HpNoco2 24 hours after pre-treatment with 100 uM DCA. Spores were counted 7 days after spray infection. Means and standard errors were calculated from three independent experiments. Mann-Whitney U test ($p<0.05$) was used to determine significant differences among mutants.
Figure 5:
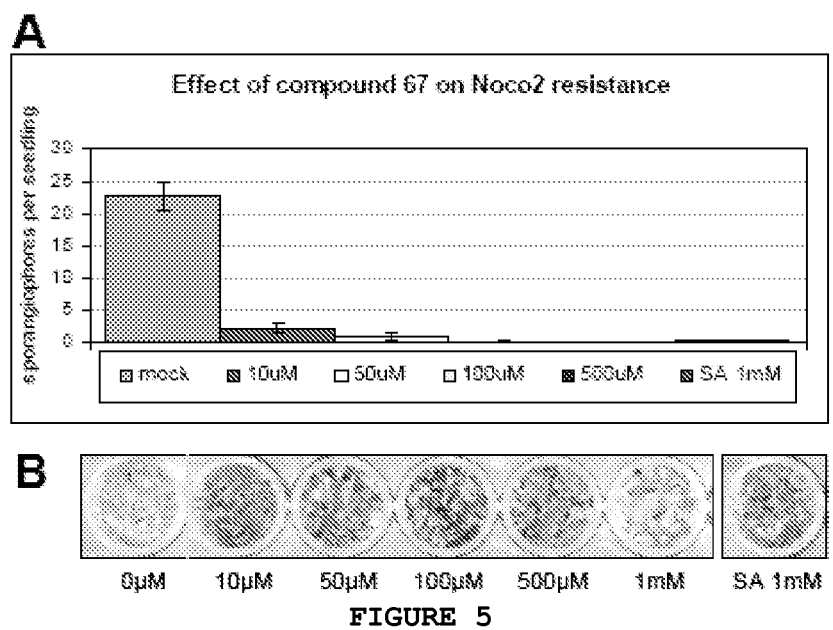
FIG. 5A-B shows that DCA induces disease resistance. A: Extent of disease susceptibility/resistance determined by counting the numbers of Peronospora sproangiophores of 17 day old seedlings 7 d after spray-inoculation with 5E4 HpNoco2 spores/ml. 24 h prior to infection with Noco2 the aerial parts of the soil grown seedlings were sprayed with the indicated concentrations of DCA (compound 67) or SA. Three replicates each with at least 30 seedlings per treatment gave similar results. B: Spraying of 10-100 uM DCA on aerial parts of –333_CaBP22::GUS seedlings induced reporter gene expression, but did not have any toxic effects on plants. Concentrations higher than 100 μM caused cell death, as indicated by reduced GUS staining.
Figure 6:
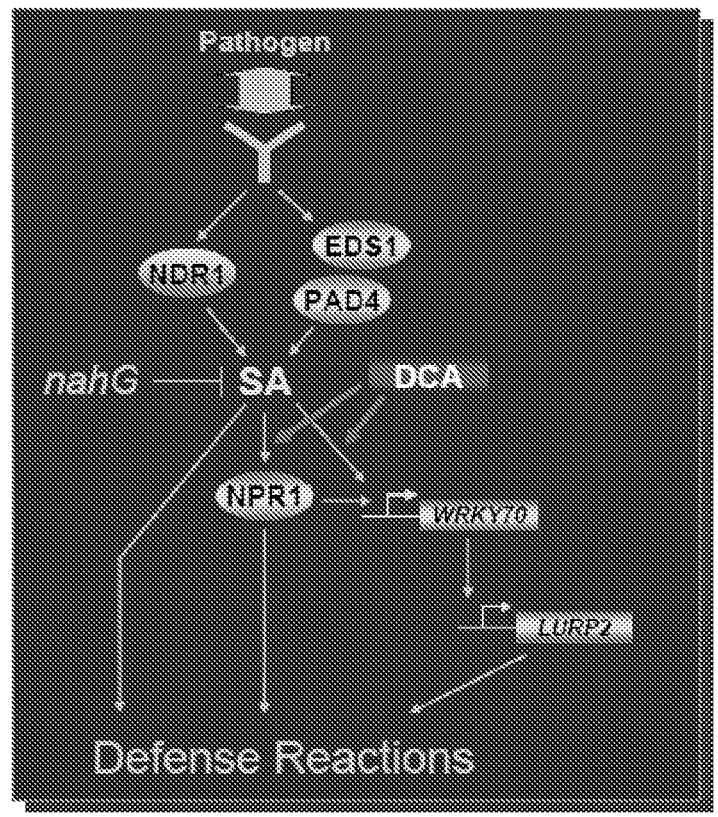
FIG. 6 is a schematic representation of the SA-dependent domain of the Arabidopsis defense signaling network. Only mutations in NPR1 and WRKY70 affect DCA-triggered responses, suggesting that this compound targets regulators operating downstream from SA, but upstream from NPR1 and WRKY70.

Consistent with this, DCA-mediated resistance to HpNoco2 was partially reduced in the wrky70 mutant (FIG. 4B). In contrast to the CaBP22 expression analyses HpNoco2 assays suggested that DCA-mediated defense reactions are also to a certain extent dependent on NPR1, as the npr1 mutant exhibits a slight reduction of DCA activity. Additional defense assays performed confirmed this. Hence, DCA seems to trigger NPR1-dependent and NPR1-independent defense responses. The latter signaling branch appears to target CaBP22 and requires WRKY70 (FIG. 4A). FIG. 4 sets forth some of these conclusions regarding the interactions of DCA with the defense signaling network.

Figure 7:
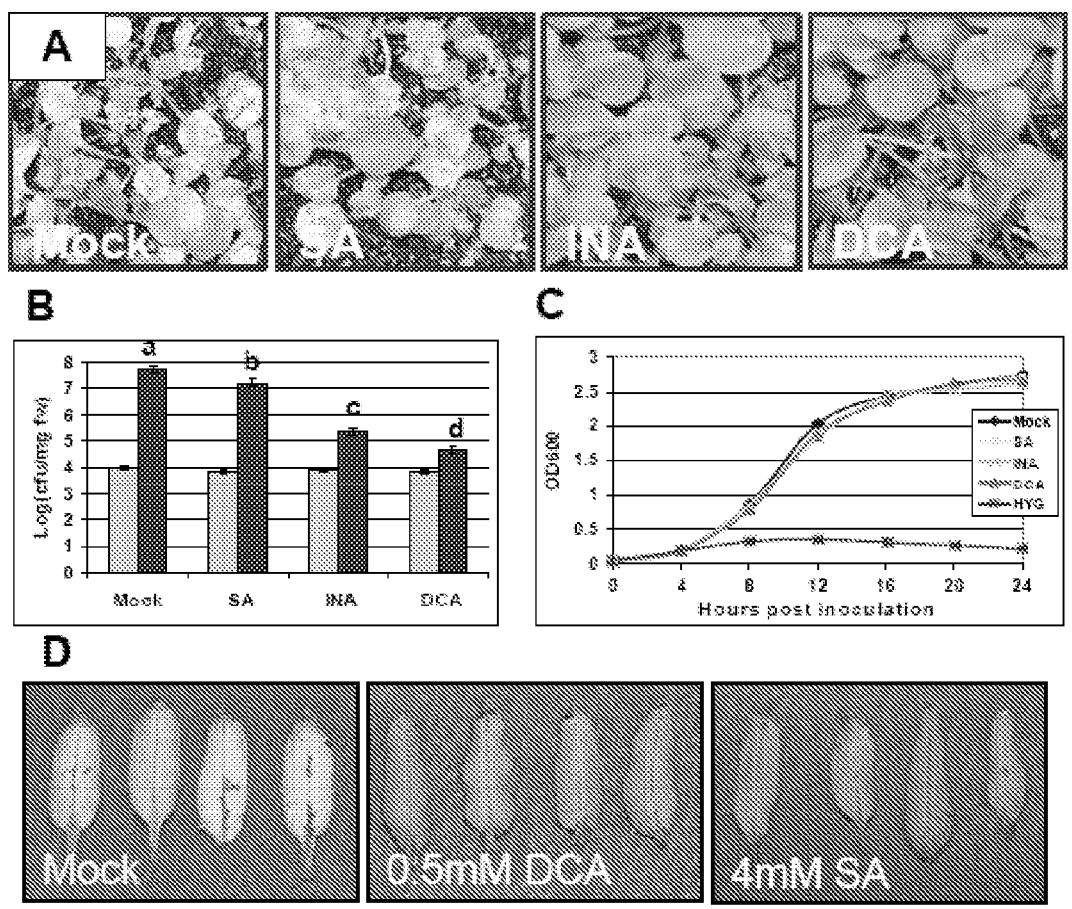
FIG. 7A-D shows that DCA induces disease resistance to virulent Pseudomonas bacteria in Arabidopsis and tomato. (A &B) 14 day old soil grown Arabidopsis Col-0 seedlings were pre-treated with 100 uM of the indicated chemical then dip inoculated with Pst DC3000. (A) Photos taken 5 dpi. (B) Quantification of Pst DC3000 growth by counting colony forming units (cfu) at day 0 (grey bars) or day 3 (black bars). Significant differences were determined by Mann-Whitney U tests ($p<0.05$). (C) Pst DC3000 grown in liquid culture with 100 um of the indicated chemicals or 100 ug/ml hygromycin (HYG). $OD_{600}$ reflecting bacterial density was measured at indicated times (hours) after inoculation. Standard errors were all less than 0.05 so are not visible on the graph. (D) Two week old cherry tomato seedlings sprayed 0.5 mM DCA, 4 mM SA or mock-treated two days prior to swab inoculation with Pst DC3000 (OD600=0.4). Photos were taken 6 days after Pst challenge.

At 100 uM DCA also triggered disease resistance to the virulent bacterial pathogen *Pseudomonas syringae* DC3000 (Pst DC3000) in *Arabidopsis* (FIGS. 7A&B). It suppressed growth of these bacteria more efficiently than SA or the frequently used SA analog INA (2,6-Dichloroisonicotinic acid; FIG. 7B). As DCA does not affect growth of Pst DC3000, when added to in vitro cultures of these bacteria (FIG. 7C), DCA-mediated suppression of bacterial growth in plants is not due to any antibiotic activity of DCA, but likely caused by its ability to induce plant defense reactions. When applied to tomato at a concentration of 500 uM, DCA suppressed Pst DC3000 mediated disease symptoms such as chlorosis (FIG. 7D), indicating that it can act as a defense inducer across species barriers (FIG. 7D).

Figure 8:
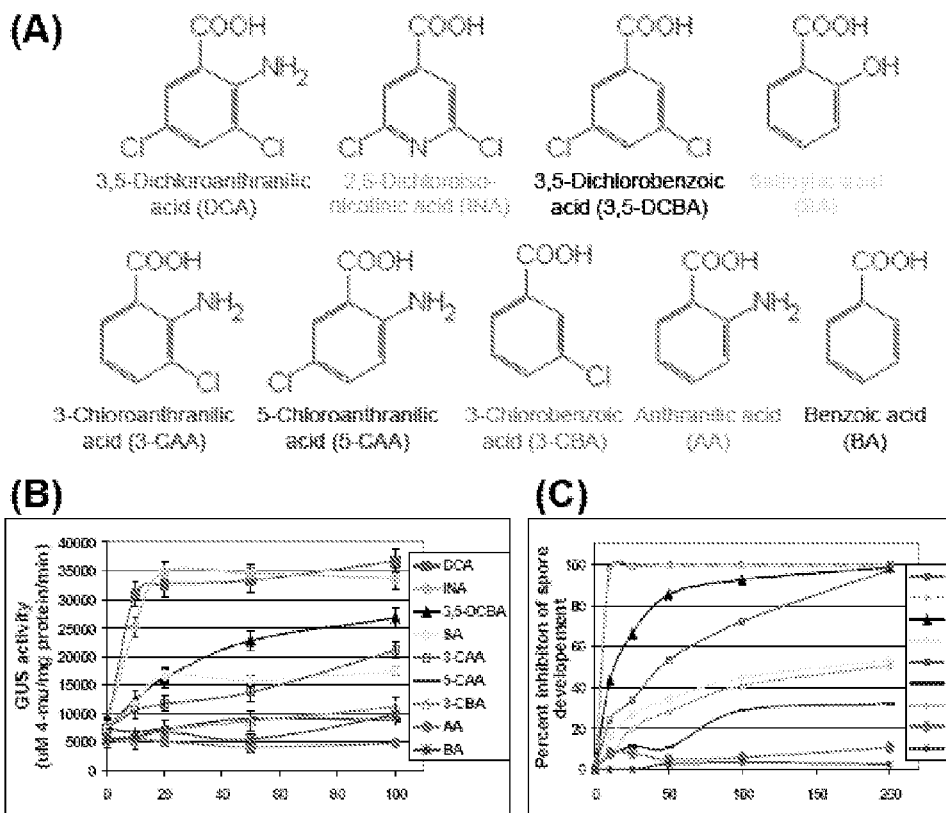
FIG. 8A-C shows structure-activity relationship analysis. (A) Chemical structures of DCA analogs analyzed. (B) Fluorometric analysis of GUS activities induced by DCA analogs. Proteins were extracted from 2 week old soil grown Col-0 seedlings 48 hours after spray-treatment with compounds at the indicated concentrations (uM). Means and standard errors calculated from 3 independent replicates. (c) HpNoco2 growth inhibition assay. 2 week old soil grown Col-0 seedlings were spray-infected with HpNoco2 48 hours after treatment with varying concentrations (uM) of each DCA analog. Seedlings were assayed 7 dpi for Peronospora growth (spore counts). 100% inhibition=0 spores. Assay was repeated three times with similar results.

DCA and the known SA-analog INA are structurally related. To compare their activities and to gain further understanding on structural features required for their defense inducing activities, a structure function analysis (SAR) was performed using multiple derivatives of DCA and INA (FIG. 8A). The efficiencies of INA and DCA in inducing −333_CaBP22::GUS expression as well as resistance to the virulent *Peronospora* isolate HpNoco2 were nearly identical (FIGS. 10B&C). All other tested compounds, including SA, triggered both defense parameters less efficiently than DCA or INA. Interestingly, the two chlorine atoms of DCA seem to be of high importance for its activity. DCA derivatives with only one chlorine atom (3-Chloroanthranilic acid and 5-Chloroanthranilic acid) exhibited reduced defense inducing activities, while those lacking chlorines, such as benzoic acid or anthranilic acid were nearly completely inactive in inducing defense responses. The activity of 4-Chloroanthranilic acid was similar to that of 5-Chloroanthranilic acid, while 6-Chloroanthranilic acid was completely inactive in the assays. The observations that DCA is more active than 3,5-Dichlorobenzoic acid and that 3-Chloroanthranilic acid is more active than 3-Chlorobenzoic acid highlights the importance of the amino group in DCA for its activity. Hence, anthranilic acid derivatives, that are chlorinated at the 3, 4 or 5 position can be considered as the simplest chemical structure capable of eliciting DCA-type biological effects. In other words, the defining feature of DCA-type synthetic elicitors are the amino group at position 2 as well as chlorines at positions 3, 4 or 5 of a benzoic acid backbone.

Figure 9:
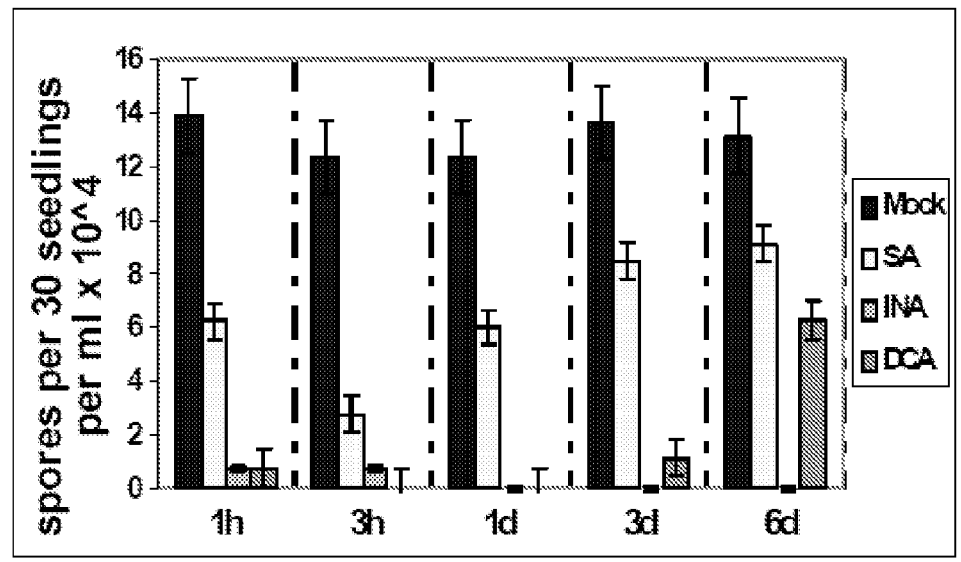
FIG. 9 shows that the defense-inducing activity of DCA is transient. DCA induces disease resistance. Time-course experiment with 2-week old Col-0 seedlings that were sprayed with 100 uM of the respective compounds at the indicated times prior to HpNoco2 ($3\times10^4$ spores/ml) spray-infection. Spores were counted 7 dpi.

Although, DCA and INA are equally efficient in inducing defense responses at 48 h after treatment, they differ substantially in their kinetic behavior (FIG. 9). DCA is only transiently active already leading to strong disease resistance by 1 h after treatment while its defense-inducing activity starts to decline between 3 and 6 days post treatment. The activity of INA lasts much longer leading to strong disease resistance for the entire duration of the experiment. This transient activity of DCA functionally discriminates it from INA and allows us to precisely correlate molecular event, such as transcriptional changes, with disease resistance. Therefore we performed a set of microarray experiments with Affymetrix ATH1 *Arabidopsis* whole genome chips profiling DCA- and INA-induced transcriptional responses at 48 h and 6 d post treatment. These analyses enabled us to identify a cluster of 131 *Arabidopsis* genes that are significantly up-regulated at 48 h post DCA or INA treatment as well as 6 d post INA treatment, but not at 6 d post DCA treatment (Table 1). The reference accession numbers and information can be used by one of skill in the art to obtain the sequences and additional information from public databases available at the time of filing. Using T-DNA mutants we are currently testing if these genes are important for disease resistance, as suggested by the strict temporal correlation of their up-regulation with disease resistance.

Based, in part, on these results, DCA is a promising lead substance for the development of pesticides designed to fight plant diseases by enhancing the plant's inherent defense capabilities. Such plant immune stimulators may prove to be superior to conventional biocidal pesticides, as they are non-toxic and expected to be more environmentally friendly. DCA is structurally and functionally distinct from other known inducers of plant immune responses, such as SA, INA and BTH. The performance of DCA may be further improvable by the design of derivatives that allow for more efficient uptake by the plant. As DCA seems to specifically target a subset of plant immune responses (an AtWRKY70-dependent signaling branch), it may prove to act in a synergistic fashion with other defense inducers that activate additional parts of the plant immune system.

TABLE 1

| AffyID | AGI | Description |
|---|---|---|
| 266761_at | AT2G47130 | short-chain dehydrogenase/reductase (SDR) family protein |
| 251705_at | AT3G56400 | member of WRKY Transcription Factor; Group III. |
| 249485_at | AT5G39020 | protein kinase family protein |
| 251232_at | AT3G62780 | C2 domain-containing protein |
| 250818_at | AT5G04930 | Encodes a putative aminophospholipid translocase (p-type ATPase) involved in chilling response. |
| 262408_at | AT1G34750 | protein phosphatase 2C, putative/PP2C |
| 259211_at | AT3G09020 | alpha 1,4-glycosyltransferase family protein/glycosyltransferase sugar-binding DXD motif-containing protein conserved region |
| 255590_at | AT4G01610 | cathepsin B-like cysteine protease, putative |
| 246293_at | AT3G56710 | Sig1 binding protein; interacts with Sig1R4. |
| 263478_at | AT2G31880 | leucine-rich repeat transmembrane protein kinase, putative |

TABLE 1-continued

| AffyID | AGI | Description |
|---|---|---|
| 249021_at | AT5G44820 | similar to unknown protein [Arabidopsis thaliana] (TAIR: AT4G19970.1) |
| 256766_at | AT3G22231 | Encodes a member of a novel 6 member Arabidopsis gene family. Expression of PCC1 is regulated by the circadian clock and is upregulated in response to both virulent and avirulent strains of Pseudomonas syringae pv. tomato. |
| 252170_at | AT3G50480 | Homolog of RPW8 |
| 246943_at | AT5G25440 | protein kinase family protein; similar to protein kinase family protein [Arabidopsis thaliana] (TAIR: AT5G11410.1); |
| 247571_at | AT5G61210 | membrane localized t-SNARE SNAP25 homologue, probably involved in cytokinesis and cell plate formation, membrane localized t-SNARE SNAP25 homologue, probably involved in cytokinesis and cell plate formation |
| 257612_at | AT3G26600 | armadillo/beta-catenin repeat family protein |
| 249797_at | AT5G23750 | remorin family protein |
| 245074_at | AT2G23200 | protein kinase family protein |
| 256100_at | AT1G13750 | calcineurin-like phosphoesterase family protein |
| 252039_at | AT3G52155 | similar to hypothetical protein TQR14A11.4 [Oryza sativa (indica cultivar-group)] (GB: AAZ06218.1) |
| 258351_at | AT3G17700 | cyclic nucleotide-binding transporter 1, member of a family of cyclic nucleotide gated channels. |
| 254032_at | AT4G25940 | epsin N-terminal homology (ENTH) domain-containing protein; Identical to Putative clathrin assembly protein At4g25940 [Arabidopsis Thaliana] (GB: Q8VYT2; GB: Q9SZG9) |
| 253993_at | AT4G26070 | Member of MAP Kinase Kinase. |
| 264223_s_at | AT3G16030 | CES101 (CALLUS EXPRESSION OF RBCS 101); carbohydrate binding/kinase |
| 267381_at | AT2G26190 | calmodulin-binding family protein |
| 257382_at | AT2G40750 | member of WRKY Transcription Factor; Group III |
| 252976s_at | AT4G38550 | similar to unknown protein [Arabidopsis thaliana] (TAIR: AT2G20950.3); similar to pEARLI 4 gene product (GB: AAC37472.1) |
| 253414_at | AT4G33050 | EDA39 (embryo sac development arrest 39) |
| 253987_at | AT4G26270 | phosphofructokinase family protein |
| 257535_at | AT3G09490 | chloroplast lumen common family protein |
| 248698_at | AT5G48380 | leucine-rich repeat family protein/protein kinase family protein; similar to leucine-rich repeat transmembrane protein kinase, putative [Arabidopsis thaliana] (TAIR: AT1G27190.1) |
| 246831_at | AT5G26340 | Encodes a protein with high affinity, hexose-specific/H+ symporter activity. |
| 253046_at | AT4G37370 | member of CYP81D, member of CYP81D |
| 256617_at | AT3G22240 | unknown protein |
| 245365_at | AT4G17720 | RNA recognition motif (RRM)-containing protein |
| 256366_at | AT1G66880 | serine/threonine protein kinase family protein |
| 254040_at | AT4G25900 | aldose 1-epimerase family protein; similar to aldose 1-epimerase family protein [Arabidopsis thaliana] (TAIR: AT5G57330.1) |
| 249486_at | AT5G39030 | protein kinase family protein; similar to protein kinase family protein [Arabidopsis thaliana] (TAIR: AT5G39020.1) |
| 247604_at | AT5G60950 | phytochelatin synthetase-related; Identical to COBRA-like protein 5 precursor (COBL5) [Arabidopsis Thaliana] (GB: Q9FME5; GB: Q6IDL3) |
| 248092_at | AT5G55170 | Encodes a small ubiquitin-like modifier (SUMO) polypeptide that becomes covalently attached to various intracellular protein targets, much like ubiquitination, leading to post-translational modification of those targets. |
| 250942_at | AT5G03350 | legume lectin family protein; similar to legume lectin family protein [Arabidopsis thaliana] (TAIR: AT3G16530.1) |
| 248945_at | AT5G45510 | leucine-rich repeat family protein; Identical to Probable disease resistance protein At5g45510 [Arabidopsis Thaliana] (GB: Q8VZC7; GB: Q9FHI5); similar to mob1/phocein family protein [Arabidopsis thaliana] (TAIR: AT4G19050.1) |
| 255116_at | AT4G08850 | leucine-rich repeat family protein/protein kinase family protein; similar to leucine-rich repeat transmembrane protein kinase, putative [Arabidopsis thaliana] (TAIR: AT1G35710.1) |
| 248970_at | AT5G45380 | sodium: solute symporter family protein |
| 255039_at | AT4G09570 | Encodes a member of Calcium Dependent Protein Kinase (CDPK) gene family. |

TABLE 1-continued

| AffyID | AGI | Description |
|---|---|---|
| 245329_at | AT4G14365 | zinc finger (C3HC4-type RING finger) family protein/ankyrin repeat family protein; similar to zinc finger (C3HC4-type RING finger) family protein/ankyrin repeat family protein [Arabidopsis thaliana] (TAIR: AT3G23280.1) |
| 264434_at | AT1G10340 | ankyrin repeat family protein; similar to ankyrin repeat family protein [Arabidopsis thaliana] (TAIR: AT2G24600.3) |
| 254500_at | AT4G20110 | vacuolar sorting receptor, putative; Identical to Vacuolar sorting receptor 7 precursor (AtVSR7) (Epidermal growth factor receptor-like protein 3) (AtELP3) (BP80-like protein f) (AtBP80f) (VSR7) [Arabidopsis Thaliana] (GB: Q8L7E3; GB: O49438) |
| 262383_at | AT1G72940 | disease resistance protein (TIR-NBS class), putative |
| 254255_at | AT4G23220 | protein kinase family protein; similar to protein kinase family protein [Arabidopsis thaliana] (TAIR: AT4G11530.1) |
| 245052_at | AT2G26440 | pectinesterase family protein |
| 250277_at | AT5G12940 | leucine-rich repeat family protein |
| 257902_at | AT3G28450 | leucine-rich repeat transmembrane protein kinase, putative |
| 262705_at | AT1G16260 | protein kinase family protein; Identical to Wall-associated receptor kinase-like 8 precursor (EC 2.7.11.-) (WAKL8) [Arabidopsis Thaliana] (GB: Q9SA25) |
| 257377_at | AT2G28890 | Encodes a protein phosphatase 2C like gene, similar to POL. Involved in leaf development. Knockout mutants have abnormally shaped leaves. |
| 245197_at | AT1G67800 | copine-related; similar to copine-related [Arabidopsis thaliana] (TAIR: AT5G14420.2) |
| 256050_at | AT1G07000 | A member of EXO70 gene family, putative exocyst subunits, conserved in land plants |
| 246405_at | AT1G57630 | disease resistance protein (TIR class), putative; similar to disease resistance protein (TIR-NBS-LRR class), putative [Arabidopsis thaliana] (TAIR: AT3G25510.1) |
| 263183_at | AT1G05570 | Encodes a callose synthase 1 catalytic subunit. Member of Glycosyltransferase Family- 48. |
| 257598_at | AT3G24800 | Contains two ring finger domains and one ZZ domain. |
| 247554_at | AT5G61010 | A member of EXO70 gene family, putative exocyst subunits, conserved in land plants. |
| 264851_at | AT2G17290 | Encodes calcium dependent protein kinase 6 (CPK6), a member of the Arabidopsis CDPK gene family. |
| 252549_at | AT3G45860 | receptor-like protein kinase, putative; similar to receptor-like protein kinase, putative [Arabidopsis thaliana] (TAIR: AT4G23310.1) |
| 261692_at | AT1G08450 | Encodes calreticulin CRT3. |
| 248327_at | AT5G52750 | heavy-metal-associated domain-containing protein; similar to heavy-metal-associated domain-containing protein [Arabidopsis thaliana] (TAIR: AT5G52760.1) |
| 248322_at | AT5G52760 | heavy-metal-associated domain-containing protein; similar to heavy-metal-associated domain-containing protein [Arabidopsis thaliana] (TAIR: AT5G52750.1) |
| 260046_at | AT1G73800 | calmodulin-binding protein; similar to calmodulin-binding protein [Arabidopsis thaliana] (TAIR: AT5G57580.1) |
| 259443_at | AT1G02360 | chitinase, putative; similar to chitinase, putative [Arabidopsis thaliana] (TAIR: AT4G01700.1); similar to chitinase precursor [Petroselinum crispum] (GB: AAD54935.1) |
| 263565_at | AT2G15390 | member of Glycosyltransferase Family- 37, member of Glycosyltransferase Family- 37 |
| 264746_at | AT1G62300 | transcription factor WRKY6 (WRKY6), transcription factor WRKY6 (WRKY6) |
| 254416_at | AT4G21380 | encodes a putative receptor-like serine/threonine protein kinases that is similar to Brassica self-incompatibility (S) locus. Expressed in root. |
| 258000_at | AT3G28940 | avirulence-responsive protein, putative/avirulence induced gene (AIG) protein, putative; similar to AIG2 (AVRRPT2-INDUCED GENE 2) [Arabidopsis thaliana] (TAIR: AT3G28930.1) |
| 265917_at | AT2G15080 | disease resistance family protein; similar to disease resistance family protein [Arabidopsis thaliana] (TAIR: AT5G27060.1) |
| 249550_at | AT5G38210 | serine/threonine protein kinase family protein |
| 248942_at | AT5G45480 | similar to unknown protein [Arabidopsis thaliana] (TAIR: AT5G45470.1) |
| 256756_at | AT3G25610 | haloacid dehalogenase-like hydrolase family protein |

TABLE 1-continued

| AffyID | AGI | Description |
|---|---|---|
| 255595_at | AT4G01700 | chitinase, putative; similar to chitinase, putative [*Arabidopsis thaliana*] (TAIR: AT1G02360.1) |
| 249417_at | AT5G39670 | calcium-binding EF hand family protein; similar to calcium-binding EF hand family protein [*Arabidopsis thaliana*] (TAIR: AT3G29000.1) |
| 252345_at | AT3G48640 | similar to unknown protein [*Arabidopsis thaliana*] (TAIR: AT5G66670.2) |
| 259495_at | AT1G15890 | disease resistance protein (CC-NBS-LRR class), putative |
| 253747_at | AT4G29050 | lectin protein kinase family protein; similar to lectin protein kinase family protein [*Arabidopsis thaliana*] (TAIR: AT1G70110.1) |
| 264951_at | AT1G76970 | VHS domain-containing protein/GAT domain-containing protein |
| 253780_at | AT4G28400 | protein phosphatase 2C, putative/PP2C, putative |
| 255913_at | AT1G66980 | protein kinase family protein/glycerophosphoryl diester phosphodiesterase family protein |
| 254869_at | AT4G11890 | protein kinase family protein; similar to EMB1290 (EMBRYO DEFECTIVE 1290), kinase [*Arabidopsis thaliana*] (TAIR: AT4G23250.1) |
| 257734_at | AT3G18370 | C2 domain-containing protein; similar to C2 domain-containing protein [*Arabidopsis thaliana*] (TAIR: AT5G11100.1) |
| 267288_at | AT2G23680 | stress-responsive protein, putative; similar to stress-responsive protein, putative [*Arabidopsis thaliana*] (TAIR: AT4G37220.1) |
| 259428_at | AT1G01560 | member of MAP Kinase, member of MAP Kinase |
| 261339_at | AT1G35710 | leucine-rich repeat transmembrane protein kinase, putative |
| 255121_at | AT4G08480 | member of MEKK subfamily, member of MEKK subfamily |
| 248568_at | AT5G49760 | leucine-rich repeat family protein/protein kinase family protein |
| 252373_at | AT3G48090 | Component of R gene-mediated disease resistance in *Arabidopsis thaliana* with homology to eukaryotic lipases. |
| 264866_at | AT1G24140 | matrixin family protein; similar to MMP (MATRIX METALLOPROTEINASE) |
| 245038_at | AT2G26560 | encodes a lipid acyl hydrolase with wide substrate specificity that accumulates upon infection by fungal and bacterial pathogens |
| 263783_at | AT2G46400 | member of WRKY Transcription Factor; Group III |
| 263584_at | AT2G17040 | ANAC036 (*Arabidopsis* NAC domain containing protein 36) |
| 249639_at | AT5G36930 | disease resistance protein (TIR-NBS-LRR class), putative |
| 260068_at | AT1G73805 | calmodulin-binding protein |
| 267490_at | AT2G19130 | S-locus lectin protein kinase family protein |
| 252346_at | AT3G48650 | pseudogene, At14a-related protein, similar to At14a (GI: 11994571 and GI: 11994573) (*Arabidopsis thaliana*) |
| 260904_at | AT1G02450 | NIMIN1 modulates PR gene expression according the following model: NPR1 forms a ternary complex with NIMIN1 and TGA factors upon SAR induction that binds to a positive regulatory cis-element of the PR-1 promoter, termed LS7. This leads to PR-1 gene induction. NIMIN1 decreases transcriptional activation, possibly through its EAR motif, which results in fine-tuning of PR-1 gene expression. |
| 254847_at | AT4G11850 | phospholipase D (gamma) |
| 254229_at | AT4G23610 | similar to unknown protein [*Arabidopsis thaliana*] (TAIR: AT3G54200.1); similar to plant cell wall protein SITFR88 [*Lycopersicon esculentum*] (GB: ABF39005.1) |
| 257101_at | AT3G25020 | disease resistance family protein |
| 248062_at | AT5G55450 | protease inhibitor/seed storage/lipid transfer protein (LTP) family protein |
| 247071_at | AT5G66640 | LIM domain-containing protein-related |
| 263539_at | AT2G24850 | Encodes a tyrosine aminotransferase that is responsive to treatment with jasmonic acid. |
| 261719_at | AT1G18380 | similar to unknown protein [*Arabidopsis thaliana*] (TAIR: AT1G67025.1) |
| 249890_at | AT5G22570 | member of WRKY Transcription Factor; Group III |
| 266782_at | AT2G29120 | member of Putative ligand-gated ion channel subunit family, member of Putative ligand-gated ion channel subunit family |
| 247602_at | AT5G60900 | Encodes a receptor-like protein kinase., Encodes a receptor-like protein kinase. |

TABLE 1-continued

| AffyID | AGI | Description |
|---|---|---|
| 246600_at | AT5G14930 | encodes an acyl hydrolase involved in senescence. |
| 253063_at | AT4G37640 | Encodes a calmodulin-regulated Ca(2+)-pump located in the endoplasmic reticulum. Belongs to plant 2B ATPase's with an N-terminal autoinhibitor. |
| 264867_at | AT1G24150 | Encodes a group I formin. Localized to cell junctions. Polymerizes actin. Binds profilin. |
| 259385_at | AT1G13470 | similar to unknown protein [*Arabidopsis thaliana*] (TAIR: AT1G13520.1) |
| 254948_at | AT4G11000 | ankyrin repeat family protein; similar to ankyrin repeat family protein [*Arabidopsis thaliana*] (TAIR: AT4G10720.1) |
| 252862_at | AT4G39830 | L-ascorbate oxidase, putative; similar to L-ascorbate oxidase, putative [*Arabidopsis thaliana*] (TAIR: AT5G21100.1) |
| 260522_x_at | AT2G41730 | similar to unknown protein [*Arabidopsis thaliana*] (TAIR: AT5G24640.1) |
| 266247_at | AT2G27660 | DC1 domain-containing protein; similar to DC1 domain-containing protein [*Arabidopsis thaliana*] (TAIR: AT2G44400.1) |
| 250751_at | AT5G05890 | UDP-glucoronosyl/UDP-glucosyl transferase family protein |
| 261161_at | AT1G34420 | leucine-rich repeat family protein/protein kinase family protein |
| 252217_at | AT3G50140 | similar to unknown protein [*Arabidopsis thaliana*] (TAIR: AT3G50130.1) |
| 254660_at | AT4G18250 | receptor serine/threonine kinase, putative |
| 249940_at | AT5G22380 | ANAC090 (*Arabidopsis* NAC domain containing protein 90) |
| 246988_at | AT5G67340 | armadillo/beta-catenin repeat family protein/U-box domain-containing protein |
| 252131_at | AT3G50930 | AAA-type ATPase family protein |
| 250796_at | AT5G05300 | unknown protein |
| 258941_at | AT3G09940 | MDHAR (MONODEHYDROASCORBATE REDUCTASE) |
| 259320_at | AT3G01080 | member of WRKY Transcription Factor; Group I |
| 256177_at | AT1G51620 | protein kinase family protein |
| 267546_at | AT2G32680 | disease resistance family protein |

Although the disclosure has been described with reference to the examples above, it should be understood that various modifications can be made without departing from the spirit of the disclosure.

What is claimed is:

1. A plant protecting composition comprising a diluent and/or carrier and a compound of general formula I:

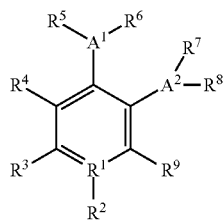

or salt thereof, wherein:
$R^1$ is C, N or S;
$R^2$ and $R^4$ are each independently a hydrogen, sulfide, alkyl, hydroxyl, alkoxide, amino, mercapto, alkyl sulfide, thionyl, halo, cyano, nitro or carboxylate;
$R^3$ and $R^9$ can be a hydrogen, alkyl, halo or mercapto, wherein at least one of $R^3$ and $R^9$ is a halogen;
$A^1$ is selected from the group consisting of a carbon, nitrogen, oxygen and sulfur; and
$A^2$ is nitrogen or —NHR$^8$ wherein R$^8$ is —H, or an alkyl;
wherein when $A^1$ or $A^2$ is a nitrogen then $R^5$, $R^6$, $R^7$ or $R^8$ is a hydrogen;
wherein when $A^1$ is a carbon then $A^1$ is either —COOH or a carboxyalkyl;
wherein the composition comprises an effective amount or concentration of the compound so as to induce modulation of a resistance gene or a gene from Table I, or induce pathogen or disease resistance in a plant; and
wherein the diluent and/or carrier is suitable for application to plants and/or seeds of plants.

2. The composition of claim 1, wherein at least one of $R^3$ or $R^9$ is a chloro-, iodo- or bromo-group.

3. The composition of claim 1, wherein the compound comprises general formula II:

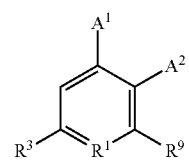

or a salt thereof, wherein:
$R^1$ is C or N;
$R^3$ and $R^9$ are each individually selected from chloro, bromo or iodo group;
$A^1$ is a —COOH or a carboxyalkyl; and
$A^2$ is —NHR$^8$ wherein R$^8$ is —H, or an alkyl.

4. The composition of claim 3, wherein the compound comprises a compound of formula III:

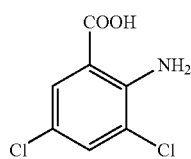

(III)

or a salt thereof.

5. The composition of claim 1, wherein the composition is formulated for foliar application, seed coating, and/or soil application.

6. The composition of claim 1, wherein the composition further comprises salicylic acid.

7. A method of providing pathogen resistance in a plant comprising contacting the plant with the composition of claim 1.

8. A method of inducing pathogen resistance in a plant comprising contacting the plant with a compound having the general formula I:

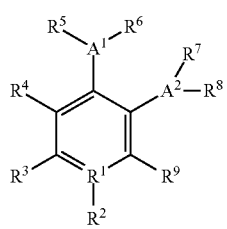

(I)

or salt thereof, wherein:
$R^1$ is C, N or S;
$R^2$ and $R^4$ are each independently a hydrogen, oxygen, sulfide, alkyl, hydroxyl, alkoxide, amino, mercapto, alkyl sulfide, thionyl, halo, cyano, nitro or carboxylate;
$R^3$ and $R^9$ can be a hydrogen, alkyl, oxygen, halo or mercapto, wherein at least one of $R^3$ and $R^9$ is a halogen;
$A^1$ is selected from the group consisting of carbon, nitrogen, oxygen and sulfur; and
$A^2$ is a nitrogen or —$NHR^8$ wherein $R^8$ is —H, or an alkyl;
wherein when $A^1$ or $A^2$ is a nitrogen, $R^5$, $R^6$, $R^7$ or $R^8$ is a hydrogen;
wherein when $A^1$ is a carbon then $A^1$ is either —COOH or a carboxyalkyl; and
wherein a structure of compound I induces modulation of a resistance gene or a gene from Table I, induces pathogen or disease resistance in a plant.

9. The method of claim 8, wherein:
$A^1$ and $A^2$ are each independently carbon or nitrogen; and
at least one of $R^3$ or $R^9$ is a chloro-, iodo- or bromo-group.

10. The method of claim 8, wherein the compound comprises general formula II:

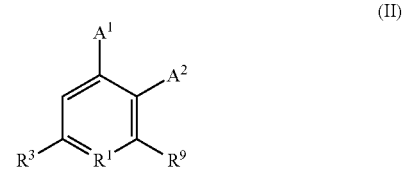

(II)

or salt thereof, wherein:
$R^1$ is C or N;
$R^3$ and $R^9$ are each individually selected from chloro, bromo or iodo group;
$A^1$ is a —COOH or a carboxyalkyl; and
$A^2$ is —$NHR^8$ wherein $R^8$ is —H, or an alkyl.

11. The method of claim 10, wherein the compound comprises a formula III:

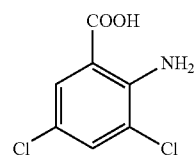

(III)

or salt thereof,
wherein the agent increases the production or transcription of a resistance gene.

12. The method of claim 8 wherein the resistance gene comprises a LURP gene member.

13. The method of claim 8 wherein the compound causes an increase in expression of LURP genes and an SA-independent constitutive expression of PR genes.

14. The composition of claim 1, wherein the compound has an effective concentration leading to half maximal response ("$EC_{50}$") of less than 10 μM for inducing pathogen or disease resistance in a plant.

15. The composition of claim 1, wherein the composition transiently induces pathogen or disease resistance in a plant from 1 hour up to 6 days after treatment.

16. The method of claim 8, wherein the compound has an effective concentration leading to half maximal response ("$EC_{50}$") of less than 10 μM for inducing pathogen or disease resistance in a plant.

* * * * *